US009578876B2

(12) United States Patent
Man et al.

(10) Patent No.: US 9,578,876 B2
(45) Date of Patent: *Feb. 28, 2017

(54) HIGHLY WETTABLE, WATER DISPERSIBLE, GRANULES INCLUDING TWO PESTICIDES

(71) Applicant: Ecolab USA Inc., St. Paul, MN (US)

(72) Inventors: Victor F. Man, St. Paul, MN (US); Yvonne M. Killeen, South St. Paul, MN (US); Susan M. Viall, Rosemount, MN (US)

(73) Assignee: Ecolab USA Inc., St. Paul, MN (US)

( * ) Notice: Subject to any disclaimer, the term of this patent is extended or adjusted under 35 U.S.C. 154(b) by 73 days.

This patent is subject to a terminal disclaimer.

(21) Appl. No.: 14/604,200

(22) Filed: Jan. 23, 2015

(65) Prior Publication Data

US 2015/0140056 A1   May 21, 2015

Related U.S. Application Data

(63) Continuation of application No. 13/272,050, filed on Oct. 12, 2011, now Pat. No. 8,968,757.

(60) Provisional application No. 61/392,353, filed on Oct. 12, 2010.

(51) Int. Cl.
A01N 25/26 (2006.01)
A01N 25/14 (2006.01)
A01N 41/02 (2006.01)
A01N 37/04 (2006.01)
A01N 37/34 (2006.01)

(52) U.S. Cl.
CPC ............. *A01N 25/26* (2013.01); *A01N 25/14* (2013.01); *A01N 37/04* (2013.01); *A01N 37/34* (2013.01); *A01N 41/02* (2013.01)

(58) Field of Classification Search
None
See application file for complete search history.

(56) References Cited

U.S. PATENT DOCUMENTS

| | | |
|---|---|---|
| 3,274,052 A * | 9/1966 | Yaffe ...................... A01N 25/26 424/421 |
| 3,808,339 A | 4/1974 | Bordenca |
| 3,873,725 A | 3/1975 | Skinner et al. |
| 3,920,442 A | 11/1975 | Albert et al. |
| 4,181,734 A | 1/1980 | D'Silva |
| 4,191,773 A | 3/1980 | Dorn |
| 4,194,001 A | 3/1980 | Ruscoe et al. |
| 4,195,080 A | 3/1980 | Herrera et al. |
| 4,198,397 A | 4/1980 | Gillings et al. |
| 4,198,782 A | 4/1980 | Kydonieus et al. |
| 4,200,644 A | 4/1980 | Engel |
| 4,206,230 A | 6/1980 | Paul |
| 4,215,138 A | 7/1980 | Ozawa et al. |
| 4,218,468 A | 8/1980 | Paul |
| 4,226,881 A | 10/1980 | Barer |
| 4,235,872 A | 11/1980 | Tocker |
| 4,235,927 A | 11/1980 | Engel |
| 4,237,168 A | 12/1980 | Reifschneider |
| 4,243,677 A | 1/1981 | Engel |
| 4,255,435 A | 3/1981 | Watkins et al. |
| 4,263,287 A | 4/1981 | Dennis |
| 4,264,606 A | 4/1981 | Ozawa et al. |
| 4,265,906 A | 5/1981 | Kasamatsu et al. |
| 4,265,907 A | 5/1981 | Paul |
| 4,268,520 A | 5/1981 | Grantham |
| 4,268,521 A | 5/1981 | Knabke |
| 4,268,525 A | 5/1981 | Paul |
| 4,271,181 A | 6/1981 | Eastburg |
| 4,279,895 A | 7/1981 | Carle |
| 4,291,055 A | 9/1981 | Chen |
| 4,291,058 A | 9/1981 | Suchy |
| 4,299,258 A | 11/1981 | Brite |
| 4,303,640 A | 12/1981 | Fuyama et al. |
| 4,308,279 A | 12/1981 | Smeltz |
| 4,313,941 A | 2/1982 | Duinker et al. |
| 4,320,139 A | 3/1982 | Takei et al. |
| 4,320,140 A | 3/1982 | Crounse et al. |
| 4,335,118 A | 6/1982 | Fischer et al. |
| 4,335,252 A | 6/1982 | Engel |
| 4,342,778 A | 8/1982 | Drabek et al. |
| 4,346,091 A | 8/1982 | Sanborn |

(Continued)

FOREIGN PATENT DOCUMENTS

CN      101326918       12/2008
EP      0 008 880 A1    3/1980

(Continued)

OTHER PUBLICATIONS

Jakasa, I. et al., "Increased permeability for polyethylene glycols through skin compromised by sodium lauryl sulphate," *Experimental Dermatology*, vol. 15, pp. 801-807 (2006).
Longman, G.F., "The analysis of detergents," *Talanta*, vol. 22, pp. 621-636 (1975).
Sinniah, B., "Insecticidal effect of aliphatic alcohols against aquatic stages of *Aedes* mosquitoes," *Transactions of the Royal Society of Tropical Medicine and Hygiene*, vol. 77, No. 1, pp. 35-38 (1983).
Sodium Lauryl Sulfate; Exemption From the Requirement of a Tolerance, *Federal Register*, vol. 74, No. 154, pp. 40503-40509 (Aug. 12, 2009).
van der Merwe, D. et al., "Effect of vehicles and sodium lauryl sulphate on xenobiotic permeability and stratum corneum partitioning in porcine skin," *Toxicology*, vol. 206, pp. 325-335 (2005).
Wadaan, M. et al., "Skin Lesions Induced by Sodium Lauryl Sulfate (SLS) in Rabbits," *J. Med. Sci.*, vol. 5, No. 4, pp. 320-323 (Oct.-Dec. 2005).

(Continued)

Primary Examiner — Robert A Wax
Assistant Examiner — Melissa Mercier
(74) Attorney, Agent, or Firm — Merchant & Gould P.C.

(57) ABSTRACT

The present disclosure relates to water dispersible granular pesticide compositions, and methods of making and using the compositions. The pesticide compositions include an inner layer including a first pesticide coated on to a substrate, and an outer layer comprising a second pesticide coated on the inner layer. The outer layer increases the water dispersibility of the granular composition, and protects the first pesticide against hydrolysis and photolysis.

20 Claims, No Drawings

(56) References Cited

U.S. PATENT DOCUMENTS

| | | |
|---|---|---|
| 4,346,092 A | 8/1982 | Sanborn |
| 4,357,348 A | 11/1982 | Kasamatsu et al. |
| 4,359,580 A | 11/1982 | Grasso |
| 4,361,554 A | 11/1982 | Saunders |
| 4,370,346 A | 1/1983 | Punja |
| 4,375,476 A | 3/1983 | Cardis |
| 4,376,785 A | 3/1983 | Matsuo et al. |
| 4,380,537 A | 4/1983 | Monroe |
| 4,382,927 A | 5/1983 | Sherman |
| 4,386,071 A | 5/1983 | Carle |
| 4,391,820 A | 7/1983 | Holan et al. |
| 4,391,823 A | 7/1983 | Boxler et al. |
| 4,393,074 A | 7/1983 | Middleton |
| 4,399,152 A | 8/1983 | Brouwer et al. |
| 4,405,353 A | 9/1983 | Angyan et al. |
| 4,415,748 A | 11/1983 | Scharpf et al. |
| 4,419,350 A | 12/1983 | Letchworth et al. |
| 4,423,028 A | 12/1983 | Walker et al. |
| 4,423,042 A | 12/1983 | Dorn et al. |
| 4,426,379 A | 1/1984 | Edwards |
| 4,436,719 A | 3/1984 | Lindaberry |
| 4,438,137 A | 3/1984 | Allan |
| 4,439,430 A | 3/1984 | Reifschneider |
| 4,447,413 A | 5/1984 | Rippstein, Jr. |
| 4,450,169 A | 5/1984 | Nezot et al. |
| 4,457,923 A | 7/1984 | Fahmy |
| 4,461,758 A | 7/1984 | Brite |
| 4,461,764 A | 7/1984 | Magee |
| 4,470,966 A | 9/1984 | Costanza et al. |
| 4,481,215 A | 11/1984 | Tocker |
| 4,490,380 A | 12/1984 | Redemann |
| 4,490,390 A | 12/1984 | Priester et al. |
| 4,496,586 A | 1/1985 | Matsui et al. |
| 4,501,742 A | 2/1985 | Harris |
| 4,504,483 A | 3/1985 | Ozawa et al. |
| 4,510,133 A | 4/1985 | Evans |
| 4,518,593 A | 5/1985 | Juvin et al. |
| 4,536,506 A | 8/1985 | Marcoux et al. |
| 4,540,710 A | 9/1985 | Holan et al. |
| 4,551,546 A | 11/1985 | Punja |
| 4,562,062 A | 12/1985 | Shinjo et al. |
| 4,564,631 A | 1/1986 | Elbert et al. |
| 4,564,639 A | 1/1986 | Nagase et al. |
| 4,567,199 A | 1/1986 | Crowley |
| 4,568,541 A | 2/1986 | Dorn et al. |
| 4,568,670 A | 2/1986 | Reifschneider et al. |
| 4,582,825 A | 4/1986 | Baumann et al. |
| 4,595,679 A | 6/1986 | Broadbent |
| 4,596,890 A | 6/1986 | Kisida et al. |
| 4,596,892 A | 6/1986 | Plummer |
| 4,602,945 A | 7/1986 | Graber et al. |
| 4,604,971 A | 8/1986 | Baker et al. |
| 4,617,316 A | 10/1986 | Plummer |
| 4,632,936 A | 12/1986 | Boase et al. |
| 4,636,523 A | 1/1987 | Plummer |
| 4,650,792 A | 3/1987 | Underwood |
| 4,659,703 A | 4/1987 | Chavdarian |
| 4,662,103 A | 5/1987 | Cheng |
| 4,666,747 A | 5/1987 | Quinn |
| 4,680,294 A | 7/1987 | Shiokawa et al. |
| 4,685,423 A | 8/1987 | Baker et al. |
| 4,688,349 A | 8/1987 | Renth |
| 4,696,822 A | 9/1987 | Matsumura et al. |
| 4,709,068 A | 11/1987 | Sieburth |
| 4,725,589 A | 2/1988 | Tsuboi et al. |
| 4,737,509 A | 4/1988 | Plummer |
| 4,767,773 A | 8/1988 | Ayad |
| 4,780,457 A | 10/1988 | Tsuboi et al. |
| 4,786,650 A | 11/1988 | Drabek |
| 4,796,381 A | 1/1989 | Kauth et al. |
| 4,798,839 A | 1/1989 | Ayad |
| 4,803,956 A | 2/1989 | Corrigan et al. |
| 4,805,341 A | 2/1989 | Maeda |
| 4,808,762 A | 2/1989 | Meier et al. |
| 4,818,525 A | 4/1989 | Kamada |
| 4,822,613 A | 4/1989 | Rodero |
| 4,826,682 A | 5/1989 | Sakharova |
| 4,833,159 A | 5/1989 | Bushell et al. |
| 4,837,209 A | 6/1989 | Chavdarian |
| 4,851,438 A | 7/1989 | Flashinski |
| 4,860,488 A | 8/1989 | Shigetoyo |
| 4,861,762 A | 8/1989 | Puritch et al. |
| 4,863,718 A | 9/1989 | Bernardo |
| 4,867,972 A | 9/1989 | Girardeau et al. |
| 4,868,209 A | 9/1989 | Punja |
| 4,873,264 A | 10/1989 | Chou et al. |
| 4,879,117 A | 11/1989 | Rombi |
| 4,888,174 A | 12/1989 | Farquharson et al. |
| 4,888,340 A | 12/1989 | Neh et al. |
| 4,889,719 A | 12/1989 | Ohtsubo et al. |
| 4,889,872 A | 12/1989 | Naumann et al. |
| 4,892,732 A | 1/1990 | Parconagian et al. |
| 4,895,871 A | 1/1990 | Lutomski et al. |
| 4,900,758 A | 2/1990 | Fisher |
| 4,904,464 A | 2/1990 | Albanese |
| 4,904,696 A | 2/1990 | Sakamoto et al. |
| 4,911,913 A | 3/1990 | Hostetter et al. |
| 4,913,893 A | 4/1990 | Varco et al. |
| 4,925,657 A | 5/1990 | Den Braber et al. |
| 4,933,181 A | 6/1990 | Brown et al. |
| 4,936,901 A | 6/1990 | Surgant, Sr. et al. |
| 4,944,950 A | 7/1990 | Sakharova |
| 4,945,088 A | 7/1990 | Okamoto et al. |
| 4,945,107 A | 7/1990 | Minetti |
| 4,956,353 A | 9/1990 | Dowd |
| 4,963,584 A | 10/1990 | Hidasi et al. |
| 4,975,425 A | 12/1990 | Barnett, Jr. |
| 4,975,451 A | 12/1990 | Cullen et al. |
| 4,980,373 A | 12/1990 | Kisida et al. |
| 4,983,391 A | 1/1991 | Muneyuki et al. |
| 4,992,275 A | 2/1991 | Lush |
| 4,997,592 A | 3/1991 | Woogerd |
| 5,017,615 A | 5/1991 | Workman |
| 5,026,727 A | 6/1991 | Bushnell |
| 5,034,404 A | 7/1991 | Uneme et al. |
| 5,049,585 A | 9/1991 | Robson et al. |
| 5,061,489 A | 10/1991 | Bernier et al. |
| 5,068,229 A | 11/1991 | Benoit et al. |
| 5,091,416 A | 2/1992 | Bushell |
| 5,100,667 A | 3/1992 | Chan et al. |
| 5,106,872 A | 4/1992 | Alder et al. |
| 5,110,594 A | 5/1992 | Morita |
| 5,122,364 A | 6/1992 | Portas |
| 5,122,518 A | 6/1992 | Vrba |
| 5,128,329 A | 7/1992 | Minagawa et al. |
| 5,152,096 A | 10/1992 | Rudolph |
| 5,153,182 A | 10/1992 | Tozzi |
| 5,166,425 A | 11/1992 | Tsushima et al. |
| 5,223,270 A | 6/1993 | Jones |
| 5,225,443 A | 7/1993 | Murphy et al. |
| 5,238,949 A | 8/1993 | Shiokawa et al. |
| 5,250,575 A | 10/1993 | Wilson et al. |
| 5,262,323 A | 11/1993 | Baird et al. |
| 5,266,324 A | 11/1993 | Stendel et al. |
| 5,300,503 A | 4/1994 | Peake et al. |
| 5,320,855 A | 6/1994 | Roche et al. |
| 5,326,560 A | 7/1994 | Henderson |
| 5,338,544 A | 8/1994 | Donovan |
| 5,352,674 A | 10/1994 | Cummings |
| 5,369,027 A | 11/1994 | Lambert et al. |
| 5,389,662 A | 2/1995 | Pap et al. |
| 5,401,771 A | 3/1995 | Demassey et al. |
| 5,427,794 A | 6/1995 | Miles |
| 5,446,019 A | 8/1995 | Ely et al. |
| 5,455,256 A | 10/1995 | Kamochi et al. |
| 5,457,178 A | 10/1995 | Jackson et al. |
| 5,476,869 A | 12/1995 | Murai et al. |
| 5,510,363 A | 4/1996 | Thirugnanam |
| 5,516,747 A | 5/1996 | Lachut |
| 5,521,192 A | 5/1996 | Henrie, II et al. |
| 5,531,981 A | 7/1996 | Kuwazuru et al. |
| 5,571,829 A | 11/1996 | Thirugnanam |
| 5,578,250 A | 11/1996 | Thomas et al. |
| 5,595,749 A | 1/1997 | Rascher et al. |

(56) References Cited

U.S. PATENT DOCUMENTS

| | | |
|---|---|---|
| 5,614,558 A | 3/1997 | James et al. |
| 5,620,678 A | 4/1997 | Burke |
| 5,631,276 A | 5/1997 | Kern |
| 5,641,499 A | 6/1997 | Bencsits |
| 5,646,133 A | 7/1997 | Sanders |
| 5,663,117 A | 9/1997 | Warner |
| 5,674,846 A | 10/1997 | Johnson et al. |
| 5,676,959 A | 10/1997 | Heitz et al. |
| 5,683,971 A | 11/1997 | Rose et al. |
| 5,702,703 A | 12/1997 | Schnepf et al. |
| 5,705,193 A | 1/1998 | Bourgogne et al. |
| 5,709,890 A | 1/1998 | Sanders et al. |
| 5,712,281 A | 1/1998 | Cullen et al. |
| 5,712,295 A | 1/1998 | Mencke et al. |
| 5,756,459 A | 5/1998 | Jackson et al. |
| 5,773,016 A | 6/1998 | Nelson |
| 5,783,203 A | 7/1998 | Schütte et al. |
| 5,792,755 A | 8/1998 | Sagenmüller et al. |
| 5,849,870 A | 12/1998 | Warren et al. |
| 5,860,266 A | 1/1999 | Martinet et al. |
| 5,885,598 A | 3/1999 | Knauf et al. |
| 5,888,989 A | 3/1999 | Kern |
| 5,910,323 A | 6/1999 | Lajoie et al. |
| 5,925,670 A | 7/1999 | Silverman et al. |
| 5,935,943 A | 8/1999 | Asai et al. |
| 5,939,438 A | 8/1999 | Yeager et al. |
| 5,942,542 A | 8/1999 | Killick et al. |
| 5,945,114 A | 8/1999 | Ogawa et al. |
| 5,977,186 A | 11/1999 | Franklin |
| 5,994,331 A | 11/1999 | Erdelen et al. |
| 5,998,330 A | 12/1999 | Felton |
| 5,998,475 A | 12/1999 | James et al. |
| 5,998,484 A | 12/1999 | Zobitne et al. |
| 6,022,881 A | 2/2000 | Asai et al. |
| 6,060,489 A | 5/2000 | Erdelen et al. |
| 6,074,656 A | 6/2000 | Katsuda et al. |
| 6,090,398 A | 7/2000 | Schroder et al. |
| 6,093,413 A | 7/2000 | Matson |
| 6,103,763 A | 8/2000 | Horst |
| 6,110,866 A | 8/2000 | Walker |
| 6,153,181 A | 11/2000 | Nelson et al. |
| 6,162,825 A | 12/2000 | Silverman et al. |
| 6,218,407 B1 | 4/2001 | Erdelen et al. |
| 6,258,369 B1 | 7/2001 | Pullen |
| 6,265,384 B1 | 7/2001 | Pearlman |
| 6,277,389 B1 | 8/2001 | Pullen |
| 6,296,865 B1 | 10/2001 | Dujardin et al. |
| 6,429,180 B1 | 8/2002 | Wisniewski et al. |
| 6,444,690 B2 | 9/2002 | Erdelen et al. |
| 6,482,863 B2 | 11/2002 | Munagavalasa et al. |
| 6,492,357 B1 | 12/2002 | Nakakura et al. |
| 6,531,163 B1 | 3/2003 | Bessette |
| 6,534,529 B2 | 3/2003 | Uhr et al. |
| 6,541,448 B2 | 4/2003 | Isaac et al. |
| 6,544,538 B1 | 4/2003 | Caine |
| 6,548,085 B1 | 4/2003 | Zobitne et al. |
| 6,564,502 B2 | 5/2003 | Barcay et al. |
| 6,576,661 B1 | 6/2003 | Brück et al. |
| 6,582,712 B2 | 6/2003 | Pullen |
| 6,582,732 B1 | 6/2003 | Bender et al. |
| 6,585,990 B1 | 7/2003 | Huang |
| 6,588,374 B1 | 7/2003 | Cottrell et al. |
| 6,593,293 B1 | 7/2003 | Baum et al. |
| 6,596,271 B2 | 7/2003 | Hammock et al. |
| 6,662,491 B2 | 12/2003 | Flinn et al. |
| 6,814,030 B2 | 11/2004 | Cottrell et al. |
| 6,849,633 B2 | 2/2005 | Okui et al. |
| 6,855,330 B2 | 2/2005 | Sirinyan et al. |
| 6,855,348 B2 | 2/2005 | Ahn et al. |
| 6,867,223 B2 | 3/2005 | Cottrell et al. |
| 6,900,190 B2 | 5/2005 | Fischer et al. |
| 6,919,090 B2 | 7/2005 | Fischer et al. |
| 6,984,662 B2 | 1/2006 | Cottrell et al. |
| 6,986,898 B1 | 1/2006 | Bessette |
| 7,019,036 B2 | 3/2006 | Hiromoto |
| 7,091,233 B2 | 8/2006 | Fischer et al. |
| 7,125,565 B2 | 10/2006 | Sugishita et al. |
| 7,132,448 B2 | 11/2006 | Cottrell et al. |
| 7,192,600 B2 | 3/2007 | Barcay et al. |
| 7,201,926 B2 | 4/2007 | Fried et al. |
| 7,205,289 B2 | 4/2007 | Fischer et al. |
| 7,208,474 B2 | 4/2007 | Bermudez et al. |
| 7,214,788 B2 | 5/2007 | Guzov et al. |
| 7,232,845 B2 | 6/2007 | Fischer et al. |
| 7,247,756 B2 | 7/2007 | Theodoridis et al. |
| 7,282,492 B2 | 10/2007 | Wengel et al. |
| 7,288,572 B2 | 10/2007 | Konze et al. |
| 7,297,351 B2 | 11/2007 | Hiromoto |
| 7,312,204 B2 | 12/2007 | Erdelen et al. |
| 7,326,704 B2 | 2/2008 | Selby |
| 7,341,735 B2 | 3/2008 | Pullen |
| 7,341,736 B2 | 3/2008 | Flashinski |
| 7,345,092 B2 | 3/2008 | Cottrell et al. |
| 7,354,595 B2 | 4/2008 | Cottrell et al. |
| 7,371,768 B2 | 5/2008 | Okui et al. |
| 7,384,647 B2 | 6/2008 | Ferko, IV |
| 7,384,927 B2 | 6/2008 | Iori |
| 7,416,880 B2 | 8/2008 | Park et al. |
| 7,423,062 B2 | 9/2008 | Tsushima |
| 7,435,411 B2 | 10/2008 | Park et al. |
| 7,439,280 B2 | 10/2008 | Lu et al. |
| 8,110,608 B2 | 2/2012 | Herrera et al. |
| 8,877,219 B2 * | 11/2014 | Bessette ............. A01N 31/04 424/405 |
| 8,968,757 B2 | 3/2015 | Man et al. |
| 2001/0014654 A1 | 8/2001 | Davister et al. |
| 2003/0073667 A1 | 4/2003 | Endris et al. |
| 2003/0092710 A1 | 5/2003 | Nakakura et al. |
| 2003/0170341 A1 | 9/2003 | Goodman et al. |
| 2004/0142903 A1 | 7/2004 | Femia et al. |
| 2004/0175405 A1 | 9/2004 | Mohamed Mahgoub et al. |
| 2005/0003001 A1 | 1/2005 | Yamaguchi et al. |
| 2005/0038094 A1 | 2/2005 | Warrington |
| 2005/0058681 A1 | 3/2005 | Johnson |
| 2005/0112165 A1 | 5/2005 | Taylor |
| 2005/0152937 A1 | 7/2005 | Lin |
| 2005/0169954 A1 | 8/2005 | Cottrell et al. |
| 2005/0196416 A1 | 9/2005 | Kipp et al. |
| 2005/0233986 A1 | 10/2005 | Clough |
| 2005/0244387 A1 | 11/2005 | Grewal |
| 2005/0244445 A1 | 11/2005 | Anderson |
| 2005/0266036 A1 | 12/2005 | Awada et al. |
| 2006/0034898 A1 | 2/2006 | Amodt et al. |
| 2006/0063829 A1 | 3/2006 | Andersch et al. |
| 2006/0083764 A1 | 4/2006 | Hernandez et al. |
| 2006/0093637 A1 | 5/2006 | Stock et al. |
| 2006/0115506 A1 | 6/2006 | Harmer et al. |
| 2006/0135564 A1 | 6/2006 | Kim et al. |
| 2006/0257440 A1 | 11/2006 | Asai et al. |
| 2007/0003586 A1 | 1/2007 | Homoelle, Jr. et al. |
| 2007/0009563 A1 | 1/2007 | Hataipitisuk |
| 2007/0048346 A1 | 3/2007 | Ido |
| 2007/0065476 A1 | 3/2007 | Sexton et al. |
| 2007/0071785 A1 | 3/2007 | Craven et al. |
| 2007/0178128 A1 | 8/2007 | Bessette |
| 2007/0202089 A1 | 8/2007 | Bermudez et al. |
| 2007/0254927 A1 | 11/2007 | Cottrell et al. |
| 2007/0254951 A1 | 11/2007 | Cottrell et al. |
| 2007/0259015 A1 | 11/2007 | Patterson et al. |
| 2007/0264297 A1 | 11/2007 | Scialdone et al. |
| 2007/0275971 A1 | 11/2007 | Erdelen et al. |
| 2007/0276014 A1 | 11/2007 | Cottrell et al. |
| 2008/0003185 A1 | 1/2008 | Valpey et al. |
| 2008/0038214 A1 | 2/2008 | Cottrell et al. |
| 2008/0038383 A1 | 2/2008 | Bessette et al. |
| 2008/0064603 A1 | 3/2008 | Pullen |
| 2008/0070787 A1 | 3/2008 | Pullen |
| 2008/0112992 A1 | 5/2008 | Mohamed Mahgoub et al. |
| 2008/0118461 A1 | 5/2008 | Boucher, Jr. et al. |
| 2008/0214400 A1 | 9/2008 | Pullen |
| 2008/0214502 A1 | 9/2008 | Smogoleski et al. |
| 2008/0214634 A1 | 9/2008 | Konze et al. |
| 2008/0233159 A1 | 9/2008 | Katsuda et al. |
| 2008/0257075 A1 | 10/2008 | Ropiak |

(56) References Cited

U.S. PATENT DOCUMENTS

| | | |
|---|---|---|
| 2008/0300225 A1 | 12/2008 | Marrone |
| 2009/0057442 A1 | 3/2009 | Nguyen |
| 2009/0082204 A1 | 3/2009 | Royalty et al. |
| 2010/0227010 A1 | 9/2010 | Jones |
| 2011/0054026 A1 | 3/2011 | Doyle et al. |
| 2012/0087987 A1 | 4/2012 | Man et al. |
| 2012/0088828 A1 | 4/2012 | Man et al. |
| 2012/0100098 A1 | 4/2012 | Herrera et al. |

FOREIGN PATENT DOCUMENTS

| | | |
|---|---|---|
| EP | 0 582 065 A1 | 2/1994 |
| EP | 0 936 859 B1 | 8/2002 |
| EP | 1 158 964 B1 | 4/2004 |
| EP | 1 490 025 B1 | 2/2008 |
| GB | 1 572 357 A | 7/1980 |
| GB | 1 604 860 A | 12/1981 |
| GB | 2 144 994 A | 3/1985 |
| GB | 2 145 086 A | 3/1985 |
| GB | 2 150 565 A | 7/1985 |
| WO | 93/22915 A1 | 11/1993 |
| WO | WO 93/22915 A1 | 11/1993 |
| WO | WO 94/22311 | 10/1994 |
| WO | WO 97/02748 | 1/1997 |
| WO | WO 01/95726 A1 | 12/2001 |
| WO | WO 2008/032328 A2 | 3/2008 |
| WO | WO 2009/147648 A2 | 12/2009 |
| WO | WO2010037503 | 4/2010 |

OTHER PUBLICATIONS

International Search Report and Written Opinion cited in International Application No. PCT/US2011/055999 mailed May 18, 2012.
Merck Index, entry 8392, for sodium lauryl sulfate, Martha Windholz, Editor (1976).
Wege, P. J., et al., "A microencapsulated formulation of lambda-cyhalothrin." Proceedings of the 3rd international conference on urban pests, 1999, pp. 301-310.
EcoEXEMP® IC2, "Insecticide Concentrate", copyright 2005 EcoSMART Technologies, Inc., pp. 1-2.
Healthy-Communications, "Sodium Lauryl Sulfate and Sodium Laureth Sulfate," <http://healthy-communications.com/slsmostdangerousirritant.html>, published Feb. 7, 2009, pp. 1-2.
Kothekar, Shrinivas C. et al., Comparative Analysis of the Properties of Tween-20, Tween-60, Tween-80, Arlacel-60, and Arlacel-80, Journal of Dispersion Science and Technology, vol. 28, pp. 477-484, (2007).
Stepanol® DX-AS165 N Product Bulletin, 2 pgs., Jan. 2008 (Stepanol Needle-form SDS Product Bulletin).
Agilent Technologies, Inc., "Fatty alcohol, C20-C28, Analysis of Fatty Alcohol in Olive Oil," (2011).

* cited by examiner

HIGHLY WETTABLE, WATER DISPERSIBLE, GRANULES INCLUDING TWO PESTICIDES

CROSS-REFERENCE TO RELATED APPLICATIONS

This application is a continuation of U.S. application Ser. No. 13/272,050 filed Oct. 12, 2011, issued as U.S. Pat. No. 8,968,757 on Mar. 3, 2015, which claims priority to Provisional Application Ser. No. 61/392,353 filed on Oct. 12, 2010, which are incorporated by reference herein in their entirety.

FIELD

The present disclosure relates generally to the field of pesticides. In particular, the present disclosure relates to highly wettable, water dispersible granules that include at least two pesticide compositions. The present disclosure also relates to methods of making and using such pesticide granules.

BACKGROUND

Left unattended, pests such as insects and rodents can quickly infest enclosed structures, such as restaurants and homes. Examples of pests which can infest areas in and around enclosed structures include cockroaches, ants, ground beetles and spiders. In addition to being a nuisance, some of these pests can also bring pathogens into the restaurant or home, creating unsanitary eating and living conditions. The use of pesticide compositions has aided in decreasing the infestation of insects in and around residential and commercial structures.

Various types of pesticide compositions and methods of repelling or terminating crawling pests are currently available, including gel baits, glue pads and poisons. Because the pests can enter walls through small cracks and crevices and inhabit relatively inaccessible areas, such as within floors and behind walls, various tools can be used to "flush" the pests from the wall. For example, flushing agents can be sprayed into the areas to irritate or agitate the pests and cause them to leave the inaccessible areas and come out into the open and expose themselves. Once the pests enter the open environment, they are exposed to a pesticide composition that terminates them.

There is an ongoing need to provide effective pesticides.

SUMMARY

In some aspects, the present disclosure relates to a granular pesticide composition comprising an inner layer comprising a first pesticide, and an outer layer comprising a second pesticide. In some embodiments, the first pesticide comprises a reduced risk pesticide. In other embodiments, a substrate is selected from the group consisting of silica particles. In other embodiments, the substrate is selected from the group consisting of soluble inerts, for example, salts and carbohydrates.

In other embodiments, the second pesticide comprises a surfactant pesticide. In some embodiments, the composition comprises a water dispersible granule. In other embodiments, the composition is substantially free of phosphorous.

In other aspects, the present disclosure relates to methods for eliminating pests comprising applying a pesticide composition to an enclosed or partially enclosed area in a structure inhabited by insects, wherein the pesticide composition comprises a water dispersible granule having an inner layer comprising a first pesticide coated on to a substrate and an outer layer comprising a second pesticide coated on the inner layer.

In some embodiments, the methods further comprise diluting the pesticide composition with a diluent before applying the pesticide composition to the enclosed or partially enclosed area. In other embodiments, the diluent comprises water.

DETAILED DESCRIPTION

In some aspects, the present disclosure relates to highly wettable, water dispersible pesticide compositions that include at least two layers, e.g., an inner layer and an outer layer, coated onto a solid substrate. Each layer includes a pesticide composition. The outer layer of pesticide is selected such that it provides an increased water wettability and dispersibility to the granules. The outer layer also aids in preventing degradation, viz., hydrolysis and/or photolysis of the inner layer of pesticide. The outer layer also improves the grease compatibility of the inner layer pesticide, and can further provide cleaning benefits. That is, in some embodiments, the outer layer can act as both a cleaning agent and an insecticide. In some embodiments, the outer layer provides pesticidal properties on contact. In some embodiments, the inner layer provides residual pesticidal properties.

So that the invention may be more readily understood certain terms are first defined.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

Compositions

In some aspects, the present disclosure relates to pesticide compositions including at least two layers. The pesticide compositions can include an inner layer, and an outer layer coated on the inner layer. The inner layer includes a first pesticide composition, and the outer layer includes a second pesticide composition. In some embodiments, the first and second pesticide compositions are not the same. In some embodiments, the first and second pesticide compositions are the same. In some embodiments, the first, second, or both the first and the second pesticide compositions are substantially free of phosphorous.

The pesticide compositions include those that kill or control a variety of pests. Pests killed or controlled by the pesticides include, but are not limited to, arthropods, e.g., insects, arachnids, crustaceans, and others. Arthropods killed or controlled by the pesticide composition include, but are not limited to, cockroaches, and any other crawling pests, for example, ants, ground beetles, spiders, bed bugs, and the like, and flying pests, and their larvae and eggs.

The inner layer includes a first pesticide composition. In some embodiments, a reduced or minimum risk pesticide, as defined by the Environmental Protection Agency ("EPA") is included as the first inner layer pesticide, but other pesticides can be used as well. Reduce risk pesticides include pesticides with characteristics such as very low toxicity to humans and non target organisms, including fish and birds, low risk of ground water contamination or runoff, and low potential for pesticide resistance. Exemplary active ingredients for reduced risk pesticides include but are not limited to, castor oil, cedar oil, cinnamon and cinnamon oil, citric acid, citronella and citronella oil, cloves and clove oil, corn gluten meal, corn oil, cottonseed oil, dried blood, eugenol, garlic and garlic oil, geraniol, geranium oil, lauryl sulfate, lemon grass oil, linseed oil, malic acid, mint and mint oil, peppermint and peppermint oil, 2-phenethyl propionate (2-phenyethyl propionate), potassium sorbate, putrescent whole egg solids, rosemary and rosemary oil, sesame and sesame oil, sodium chloride, sodium lauryl sulfate, soybean oil, thyme and thyme oil, white pepper, zinc metal strips, and combinations thereof. Examples of other pesticides that can be used in the inner layer include TEMPO® Ultra WP and TEMPO Ultra SC, commercially available from Bayer Professional Care, Suspend SC, available from Bayer Environmental Science, Phantom, available from BASF, Talstar Pro, available from FMC, and Demand CS, available from Syngenta.

In some embodiments, the inner layer includes an effective amount of a pesticide, viz., an amount effective to kill or control a targeted pest, e.g., insect. In some embodiments, the first inner layer includes about 1 wt % to about 90 wt %, about 20 wt % to about 80 wt %, or about 30 wt % to about 60 wt % of a pesticide.

In some embodiments, the first pesticide composition includes a pesticide that has poor grease compatibility. As used herein the term "poor grease compatibility" refers to compounds and compositions that are hydrophobic and lipophilic, and tend to migrate into the grease layer that they come into contact with. Thus, they are not as efficacious against pests as those pesticides which have higher grease compatibilities. In some embodiments, the first pesticide composition is a residual kill pesticide.

The inner layer can be coated onto a substrate. Any substrate capable of being coated with a first pesticide composition can be used. For example, in some embodiments, an insoluble material, e.g., silica particles can be used as the substrate for coating a first pesticide composition on to. In other embodiments, a soluble material, e.g., salts and/or carbohydrates can be used as the substrate. Examples include sodium chloride, sodium acetate, sodium bicarbonate, sodium sesquicarbonate, sodium carbonate, sodium sulfate, trisodium phosphate, disodium phosphate, monosodium phosphate, sodium tripolyphosphate, potassium chloride, potassium acetate, potassium carbonate, sugar, sucrose, and the like. Any material capable of having the first pesticide applied to it can be used as a substrate. Preferred substrates are about 50 microns in diameter or smaller for insoluble substrates.

In other embodiments, the inner layer can be formed by an agglomeration or granulation process.

In other embodiments, a pre-formed first pesticide composition is used as the inner layer already coated on a substrate. For example, a commercially available pesticide available for use in a solid form can be used. In some embodiments, the first pesticide composition comprises a solid form of a reduced risk pesticide as defined by the EPA, but pesticides that do not qualify as reduced risk can also be used.

In some aspects, the outer layer of the pesticide composition includes a second pesticide composition. In some embodiments, the second pesticide composition is a contact kill pesticide when dissolved in water that kills pests or insects on contact. In some embodiments, the second pesticide composition includes a surfactant pesticide. As used herein, the term "surfactant pesticide" refers to a pesticide which also has surfactant properties. That is, a surfactant pesticide refers to a chemical substance which has the ability to kill or control pests, e.g., insects, and also has the ability to reduce or lower the surface tension of a liquid with which the surfactant pesticide comes into contact with. Preferred surfactant pesticides include sodium lauryl sulfate, alcohol ethoxylates, quaternary ammonium compounds, fatty acids, fatty acid soaps, twin-tailed surfactants such as dioctylsulfosuccinate, and mixtures thereof. Preferred surfactant pesticides include a hydrophobic portion with from about 6 to about 16 carbon atoms, or about 8 to 14, or about 10 to 12 carbon atoms. In some embodiments, the surfactant pesticide includes sodium lauryl sulfate. Sodium lauryl sulfate is a surfactant pesticide that is highly soluble in water, e.g., 250 g/L at 20° C.

In other embodiments, the second pesticide composition includes a combination of surfactant pesticide and water. The combination of surfactant pesticide and water can be sprayed on to the inner layer to form the outer layer of the composition, and upon drying form granules. For example, in some embodiments, the second pesticide composition can include a combination of a solid form of surfactant pesticide and water. Suitable component concentrations for a concentrate of the second pesticide composition include between about 40% and about 100%, between about 50% and about 100%, between about 60% and 100%, between about 70% and between about 100%, between about 80% and 100%, between about 90% and about 100%, between about 93% and about 100%, or between about 95% and about 100% surfactant pesticide by weight and balance water.

Examples of suitable solid forms of sodium lauryl sulfate include, but are not limited to, powder, pellet and block forms. An example of a particularly suitable pellet form of sodium lauryl sulfate is needle form sodium lauryl sulfate. An example of a suitable commercially available needle form sodium lauryl sulfate includes Stepanol DX®, CAS number 151-21-3, available from Stephan Company, Northfield, Ill. While both powder form and pellet form sodium lauryl sulfate may be used to form the pesticide composition of the present invention, pellet form sodium lauryl sulfate is generally easier to handle and does not become airborne as easily as other solid forms.

In other embodiments, a commercially available aqueous solution of a surfactant can be used, for example, a 30% sodium lauryl sulfate.

In further embodiments, the pesticide composition may also include additional components or agents, such as additional functional materials. In other embodiments, the first and second pesticides of the pesticide composition may provide a large amount, or even all of the total weight of the pesticide composition, for example, in embodiments having few or no additional functional materials disposed therein.

The functional materials provide desired properties and functionalities to the pesticide composition. For the purpose of this application, the term "functional materials" includes a material that when dispersed or dissolved in a use and/or concentrate solution, such as an aqueous solution, or when included in granules of the present invention, provides a beneficial property in a particular use. Some particular examples of functional materials are discussed in more detail below, although the particular materials discussed are given by way of example only, and a broad variety of other functional materials may be used.

The pesticide compositions may include attractants such as cockroach pheromones (e.g., sex attractants, aggregation pheromones) or food-based attractants (e.g., methylcyclopentenalone, maltol, fenugreek and other flavorings). When an attractant is included in the pesticide compositions, the attractant may constitute between about 0.1% and about 5% by weight of the pesticide composition. The pesticide compositions may also optionally include humectants such as glycerol to slow evaporation and maintain wetness of the pesticide composition after application. When a humectant is included in the pesticide composition, the humectant may constitute between about 0.5% and about 10% by weight of the pesticide composition.

In some embodiments, the pesticide compositions can also include a co-surfactant. Without wishing to be bound by any particular theory, it is thought that the inclusion of a co-surfactant composition can reduce the drying of the second pesticide composition, and prolong the activity of the pesticide composition. Further, it is thought that the inclusion of a co-surfactant can increase the insecticidal efficacy of the compositions. When a co-surfactant composition is included, the co-surfactant composition can be present at a ratio of up to about 1:0.03, 1:0.5, 1:1, or 1:3 of the surfactant pesticide to the co-surfactant composition. Exemplary co-surfactants include long-chain alcohols, amine oxides, guerbet alcohols, guerbet alcohol ethoxylates, protonated fatty acids, and twin-tailed surfactants such as dioctylsulfosuccinate. The co-surfactants preferably have a hydrophobic tail with a carbon chain length of from about 6 to 16, about 8 to 14, or about 10 to 12.

The compositions can also include additional inert ingredients. In some embodiments, the compositions include only additional inert ingredients that can be included in reduced/minimum risk pesticide products exempted under Section 25(b) of the Federal Insecticide, Fungicide, and Rodenticide Act ("FIFRA").

Methods of Making and Using

The water dispersible granules may be made by a variety of processes. In some aspects, the outer layer can be sprayed or melted on to the inner layer. In some aspects, the water dispersible granules may be made using an agglomeration process, or a fluidized bed process. For example, a substrate, e.g., silica particles or a water soluble salt, can be suspended in a fluidized bed. A solution of the first pesticide composition in a carrier can then be sprayed on to the suspended substrate particles. After the first pesticide composition is coated on to the substrate, the second pesticide composition is sprayed on to the coated substrate. In some embodiments, the second pesticide composition includes sodium lauryl sulfate and water.

In other aspects, a first pesticide composition already pre-formed can be used. That is, a commercially available pesticide composition in a solid form, e.g., granules or powders, can be used. To make compositions according to embodiments of the present invention, a second pesticide composition, e.g., sodium lauryl sulfate can be coated on to the first pesticide composition.

In some aspects, the present disclosure relates to methods for eliminating pests. The methods include applying the pesticide compositions to an enclosed or partially enclosed area in a structure inhabited by pests.

The pesticide compositions can be applied to the area to be treated in a variety of ways. In some embodiments, the granules are applied to the area using a drop type, rotary type, or hand held type applicator. In other embodiments, the pesticide composition granules can be dissolved in a carrier, e.g., water, at the location of use to provide a use solution. Once the pesticide composition has been thoroughly dispersed in the carrier to form a substantially homogeneous or uniform solution, the pesticide composition may be applied onto a surface as a spray or foam. The use solution is applied onto the surface for an amount of time sufficient to terminate the pests.

The pesticide compositions may be employed at any of a wide variety of locations in which it is desired to eliminate pest infestation. The pesticide compositions are effective in killing pests, including crawling and flying pests, and in particular cockroaches. In addition, the pesticide compositions are generally more ecologically sustainable than traditional pesticides, making it particularly useful where it is desired to use an environmentally friendly pesticide. Such applications include using the pesticide compositions in and around restaurants, stores, homes, or other generally enclosed structures in which humans and animals are present.

The pesticide compositions can be applied in and around areas such as apartment buildings, bakeries, beverage plants, bottling facilities, breweries, cafeterias, candy plants, canneries, cereal processing and manufacturing plants, cruise ships, dairy barns, poultry facilities, flour mills, food processing plants, frozen food plants, homes hospitals, hotels, houses, industrial buildings, kennels, kitchens, laboratories, manufacturing facilities, mausoleums, meat processing and packaging plants, meat and vegetable canneries, motels, nursing homes, office buildings, organic facilities, restaurants, schools, stores, supermarkets, warehouses and other public buildings and similar structures. In particular, the pesticide compositions can be applied to surfaces, such as floors, where pests may harbor, including cracks, crevices, niches, dark areas, drains, and other harborage sites.

The pesticide compositions can also be used in methods for controlling insects, arachnids, and mites. The method includes allowing an effective amount of the pesticide compositions to act on the insects, arachnids, and/or mites.

The present disclosure may be better understood with reference to the following examples. These examples are intended to be representative of specific embodiments of the disclosure, and are not intended as limiting the scope of the disclosure.

EXAMPLES

Example 1

Example 1 tested the pesticidal efficacy of a granule with an inner layer pesticide and an outer layer pesticide. The example first looked at the pesticidal properties in a wet panel forced exposure test to determine the efficacy of the pesticide on contact. Then the example looked at the pesticidal properties in a dry panel forced exposure test to determine the residual efficacy of the pesticide.

For the wet panel forced test, 20 adult male German cockroaches are placed on a stainless steel panel. The panel with the cockroaches are placed in a spray tower and sprayed with the pesticide for 60 seconds, starting when the spray comes into contact with the surface of the panel. The cockroaches are removed from the panel and placed in a jar with food and water. The jar is then observed for mortality at certain time intervals post-exposure.

For the dry panel test, panels are prepared by spraying the pesticide on the panel and allowing the panel to dry. Then 20 adult male German cockroaches are placed on the panel and allowed to remain on the panel for 60 seconds. The cockroaches are removed from the panel and placed in a jar with food and water. The jars are observed for mortality at certain time intervals post-exposure. The dry forced exposure tests suggests how the pesticides would perform as a residual pesticide.

TABLE 1

Mortality Over Time Using the Wet Forced Exposure Test

|  | 1 min. | 5 min. | 15 min. | 30 min. | 1 hour | 2 hours | 24 hours |
|---|---|---|---|---|---|---|---|
| Dried up Finito + Tempo WP | 83.33 | 100 | 100 | 100 | 100 | 100 | 100 |
| SLS + decyl alcohol + Tempo WP | 31.67 | 65 | 100 | 100 | 100 | 100 | 100 |
| Tempo WP | 8.33 | 25 | 100 | 100 | 100 | 100 | 100 |
| Water | 0 | 0 | 0 | 0 | 0 | 0 | 0 |

Table 1 shows that a granule with dried up Finito as the outer layer (Finito is an aqueous pesticide commercially available from Ecolab Inc., St. Paul, Minn.) plus Tempo WP as the inner layer (a pesticide commercially available from Bayer Professional Care) (final dried composition is 98.8% dried Finito Solid and 5.2% Tempo WP; test solution was made by dispersing 9.45 grams of the dried composition in 90.55 grams of deionized water) was effective against 83.33% of the cockroaches within 1 minute, and 100% within 5 minutes. Also, a granule with SLS and decyl alcohol as the outer layer and Tempo WP as the inner layer (final dried composition was 48.61% SLS, 2.93% decyl alcohol, and 48.46% Tempo WP; test solution was made by dispersing 0.6 gram of the dried composition in 99.4 grams of deionized water) was effective against 31.67% of the cockroaches within 1 minute, and 65% within 5 minutes. Both are providing significantly improved contact kill in comparison to Tempo WP, which was effective against 0% of the cockroaches within 1 minute, and 25% within 5 minutes.

TABLE 2

Mortality Over Time Using the Dry Forced Panel Test

|  | 1 Min | 24 Hour | 48 Hour | 72 Hour | 1 Week |
|---|---|---|---|---|---|
| Dried up Finito + Tempo WP | 48.33 | 33.33 | 30.00 | 51.67 | 51.67 |
| SLS + decyl alcohol + Tempo WP | 100.00 | 100.00 | 100.00 | 100.00 | 100.00 |
| Tempo WP | 100.00 | 100.00 | 100.00 | 100.00 | 100.00 |
| Water | 0.00 | 0.00 | 0.00 | 0.00 | 0.00 |

OTHER EMBODIMENTS

It is to be understood that while the invention has been described in conjunction with the detailed description thereof, the foregoing description is intended to illustrate, and not limit the scope of the invention, which is defined by the scope of the appended claims. Other aspects, advantages, and modifications are within the scope of the following claims.

In addition, the contents of all patent publications discussed supra are incorporated in their entirety by this reference.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

We claim:

1. A granular pesticide composition comprising:
   (a) an inner layer comprising a first pesticide; and
   (b) an outer layer comprising a second pesticide, wherein the second pesticide is a surfactant pesticide with a hydrophobic portion with a carbon chain length of from about 6 to about 16.

2. The composition of claim 1, wherein the first pesticide comprises a reduced risk pesticide.

3. The composition of claim 1, wherein the first pesticide is coated on a substrate selected from the group consisting of silica particles, inert soluble materials, salts, carbohydrates, and combinations thereof.

4. The composition of claim 1, wherein the surfactant pesticide is selected from the group consisting of sodium lauryl sulfate, alcohol ethoxylates, quaternary ammonium compounds, fatty acids, fatty acid soaps, dioctylsulfosuccinate, and mixtures thereof.

5. The composition of claim 1, wherein the composition comprises a water dispersible granule.

6. The composition of claim 1, wherein the composition is substantially free of phosphorous.

7. The composition of claim 2, wherein the reduced risk pesticide comprises an active ingredient selected from the group consisting of castor oil, cedar oil, cinnamon and cinnamon oil, citric acid, citronella and citronella oil, cloves and clove oil, corn gluten meal, corn oil, cottonseed oil, dried blood, eugenol, garlic and garlic oil, geraniol, geranium oil, lauryl sulfate, lemon grass oil, linseed oil, malic acid, mint and mint oil, peppermint and peppermint oil, 2-phenethyl propionate (2-phenyethyl propionate), potassium sorbate, putrescent whole egg solids, rosemary and rosemary oil, sesame and sesame oil, sodium chloride, sodium lauryl sulfate, soybean oil, thyme and thyme oil, white pepper, zinc metal strips, and combinations thereof.

8. The composition of claim 1, wherein the second pesticide further comprises an active ingredient selected from the group consisting of castor oil, cedar oil, cinnamon and cinnamon oil, citric acid, citronella and citronella oil, cloves and clove oil, corn gluten meal, corn oil, cottonseed oil, dried blood, eugenol, garlic and garlic oil, geraniol, geranium oil, lauryl sulfate, lemon grass oil, linseed oil, malic acid, mint and mint oil, peppermint and peppermint oil, 2-phenethyl propionate (2-phenyethyl propionate), potassium sorbate, putrescent whole egg solids, rosemary and rosemary oil, sesame and sesame oil, sodium chloride, sodium lauryl sulfate, soybean oil, thyme and thyme oil, white pepper, zinc metal strips, and combinations thereof.

9. The composition of claim 1, wherein the first pesticide is a residual pesticide and the second pesticide is a contact kill pesticide.

10. The composition of claim 1, wherein the second pesticide further comprises a co-surfactant selected from the group consisting of long-chain alcohols, amine oxides, guerbet alcohols, guerbet alcohol ethoxylates, protonated fatty acids, dioctylsulfosuccinate and mixtures thereof, and the co-surfactant has a hydrophobic portion with a carbon chain length of from about 6 to 16.

11. A method for eliminating pests comprising: applying the pesticide composition of claim 1 to an enclosed or partially enclosed area in a structure inhabited by insects.

12. The method of claim 11, wherein the first pesticide comprises a reduced risk pesticide.

13. The method of claim 11, wherein the pesticide composition comprises a water dispersible granule comprising a substrate, and wherein the substrate is selected from the group consisting of silica particles.

14. The method of claim 11, wherein the surfactant pesticide comprises sodium lauryl sulfate.

15. The method of claim 11, wherein the pesticide composition is substantially free of phosphorous.

16. The method of claim 12, wherein the reduced risk pesticide comprises an active ingredient selected from the group consisting of castor oil, linseed oil, cedar oil, malic acid, cinnamon, cinnamon oil, mint, mint oil, citric acid, peppermint, peppermint oil, citronella, citronella oil, 2-phenethyl propionate, cloves, clove oil, potassium sorbate, corn gluten meal, putrescent whole egg solids, corn oil, rosemary, rosemary oil, cottonseed oil, sesame, sesame oil, dried blood, sodium chloride, eugenol garlic, garlic oil, soybean oil, geraniol, thyme, thyme oil, geranium oil, white pepper, lauryl sulfate, lemongrass oil, and mixtures thereof.

17. The method of claim 11, wherein the second pesticide further comprises an active ingredient selected from the group consisting of castor oil, linseed oil, cedar oil, malic acid, cinnamon, cinnamon oil, mint, mint oil, citric acid, peppermint, peppermint oil, citronella, citronella oil, 2-phenethyl propionate, cloves, clove oil, potassium sorbate, corn gluten meal, putrescent whole egg solids, corn oil, rosemary, rosemary oil, cottonseed oil, sesame, sesame oil, dried blood, sodium chloride, eugenol garlic, garlic oil, soybean oil, geraniol, thyme, thyme oil, geranium oil, white pepper, lauryl sulfate, lemongrass oil, and mixtures thereof.

18. The method of claim 11, further comprising diluting the pesticide composition with a diluent before applying the pesticide composition to the enclosed or partially enclosed area.

19. The method of claim 18, wherein the diluent comprises water.

20. A granular pesticide composition comprising:
(a) an inner layer comprising a first pesticide combined with an inert substrate, wherein the pesticide is a residual kill pesticide; and
(b) an outer layer comprising a second pesticide coated on to the inner layer, wherein the second pesticide is a contact kill pesticide comprising
a surfactant pesticide selected from the group consisting of sodium lauryl sulfate, alcohol ethoxylates, quaternary ammonium compounds, fatty acids, fatty acid soaps, dioctylsulfosuccinate, and mixtures thereof and the surfactant pesticide has a hydrophobic portion with a carbon chain length of from about 6 to 16; and
a co-surfactant selected from the group consisting of long-chain alcohols, amine oxides, guerbet alcohols, guerbet alcohol ethoxylates, protonated fatty acids, dioctylsulfosuccinate and mixtures thereof, and the co-surfactant has a hydrophobic portion with a carbon chain length of from about 6 to 16.

* * * * *

UNITED STATES PATENT AND TRADEMARK OFFICE
CERTIFICATE OF CORRECTION

Page 1 of 1

PATENT NO. : 9,578,876 B2
APPLICATION NO. : 14/604200
DATED : February 28, 2017
INVENTOR(S) : Man et al.

It is certified that error appears in the above-identified patent and that said Letters Patent is hereby corrected as shown below:

In the Claims

Column 9, Line 7, Claim 7: "propionate (2-phenyethyl propionate)," should read --propionate (2-phenylethyl propionate),--

Column 9, Line 20, Claim 8: "propionate (2-phenyethyl propionate)," should read --propionate (2-phenylethyl propionate),--

Signed and Sealed this
Twenty-eighth Day of April, 2020

Andrei Iancu
*Director of the United States Patent and Trademark Office*